United States Patent [19]

Hashi et al.

[11] Patent Number: 5,302,701
[45] Date of Patent: Apr. 12, 1994

[54] POLYPEPTIDE HAVING HUMAN FIBRONECTIN-LIKE CELL ADHESIVE ACTIVITY

[75] Inventors: Hidetaka Hashi, Ibaraki; Fusao Kimizuka, Ohmihachiman; Ikunoshin Kato, Uji; Mika Hatai, Tokyo; Yoshihito Yaoi, Yokohama, all of Japan

[73] Assignee: Takara Shuzo Co., Ltd., Kyoto, Japan

[21] Appl. No.: 959,369

[22] Filed: Oct. 13, 1992

[30] Foreign Application Priority Data

Oct. 14, 1991 [JP] Japan ............... 3-291959
Mar. 5, 1992 [JP] Japan ............... 4-83220

[51] Int. Cl.$^5$ .................. A61K 35/14; C07K 13/00
[52] U.S. Cl. .................. 530/399; 530/382;
530/350; 530/395; 530/830; 530/402; 530/404;
530/405; 530/406; 530/380
[58] Field of Search ............ 530/382, 395, 399, 402, 530/404, 405, 406, 830, 380; 514/12

[56] References Cited

U.S. PATENT DOCUMENTS

| | | | |
|---|---|---|---|
| 4,440,860 | 4/1984 | Klagsbrun | 435/240.3 |
| 4,587,122 | 5/1986 | Kagitani et al. | 514/21 |
| 5,045,631 | 9/1991 | Kimizuka et al. | 530/350 |
| 5,049,658 | 9/1991 | Kimizuka et al. | 530/350 |
| 5,078,744 | 1/1992 | Chvapil | 623/13 |
| 5,102,988 | 4/1992 | Kimizuka et al. | 530/350 |
| 5,136,023 | 8/1992 | Hashino et al. | 530/350 |
| 5,151,412 | 9/1992 | Brown | 514/8 |
| 5,171,318 | 9/1992 | Gibson et al. | 623/5 |

FOREIGN PATENT DOCUMENTS 0237966 9/1987 European Pat. Off. .
3-232898 10/1991 Japan .

OTHER PUBLICATIONS

Ann. Rev. Biochemistry, 57, 375–413 (1988).
The EMBO Journal, 4, 1755–1759 (1985).
Biochemistry, 25, 4936–4941 (1986).
Ann. Rev. Biochemistry, 58, 575–606 (1989).
The EMBO Journal, 5, 2523–2528 (1986).
Chemical Abstracts vol. 113:57494v (1989).
Chemical Abstracts vol. 115:86745z (1991).

Primary Examiner—Michael G. Wityshyn
Assistant Examiner—C. Sayala
Attorney, Agent, or Firm—Wenderoth, Lind & Ponack

[57] ABSTRACT

This present invention is directed to an artificial functional polypeptide represented by the following structural formula [I]:

$$X\text{—}(Y)_m\text{—}Z \qquad [I]$$

wherein X represents a polypeptide having cell-adhesive activity like that of human FN, Y represents a spacer, Z represents a polypeptide having fibroblast growth promoting activity like that of FGF, and m is 1 or 0. This polypeptide is particularly useful for pharmaceutical purposes.

1 Claim, 1 Drawing Sheet

SEQUENCE LISTING ( 1 ) GENERAL INFORMATION:

(i i i) NUMBER OF SEQUENCES: 23

(2) INFORMATION FOR SEQ ID NO:1:

(i) SEQUENCE CHARACTERISTICS:
        (A) LENGTH: 256 amino acids
        (B) TYPE: amino acid
        (C) STRANDEDNESS: single
        (D) TOPOLOGY: linear (i i) MOLECULE TYPE: polypeptide (i i i) HYPOTHETICAL:

(i v) ANTI-SENSE:

(v) FRAGMENT TYPE:

(v i) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(v i i) IMMEDIATE SOURCE:
        (A) LIBRARY:
        (B) CLONE:

(v i i i) POSITION IN GENOME:
        (A) CHROMOSOME/SEGMENT:
        (B) MAP POSITION:
        (C) UNITS:

(i x) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(x i) SEQUENCE DESCRIPTION: SEQ ID NO:1:

```
Pro  Ser  Ile  Asp  Leu  Thr  Asn  Phe  Leu  Val  Arg  Tyr  Ser  Pro  Val
 1              5                        10                        15

Lys  Asn  Glu  Glu  Asp  Val  Ala  Glu  Leu  Ser  Ile  Ser  Pro  Ser  Asp
                20                        25                        30

Asn  Ala  Val  Val  Leu  Thr  Asn  Leu  Leu  Pro  Gly  Thr  Glu  Tyr  Val
                35                        40                        45

Val  Ser  Val  Ser  Ser  Val  Tyr  Glu  Gln  His  Glu  Ser  Thr  Pro  Leu
                50                        55                        60

Arg  Gly  Arg  Gln  Lys  Thr  Gly  Leu  Asp  Ser  Pro  Thr  Gly  Ile  Asp
                65                        70                        75

Phe  Ser  Asp  Ile  Thr  Ala  Asn  Ser  Phe  Thr  Val  His  Trp  Ile  Ala
                80                        85                        90

Pro  Arg  Ala  Thr  Ile  Thr  Gly  Tyr  Arg  Ile  Arg  His  His  Pro  Glu
                95                       100                       105
```

-continued

| | | | | | | | | | | | | |
|---|---|---|---|---|---|---|---|---|---|---|---|---|
| His | Phe | Ser | Gly | Arg<br>110 | Pro | Arg | Glu | Asp | Arg<br>115 | Val | Pro | His | Ser | Arg<br>120 |

| Asn | Ser | Ile | Thr | Leu<br>125 | Thr | Asn | Leu | Thr | Pro<br>130 | Gly | Thr | Glu | Tyr | Val<br>135 |

| Val | Ser | Ile | Val | Ala<br>140 | Leu | Asn | Gly | Arg | Glu<br>145 | Glu | Ser | Pro | Leu | Leu<br>150 |

| Ile | Gly | Gln | Gln | Ser<br>155 | Thr | Val | Ser | Asp | Val<br>160 | Pro | Arg | Asp | Leu | Glu<br>165 |

| Val | Val | Ala | Ala | Thr<br>170 | Pro | Thr | Ser | Leu | Leu<br>175 | Ile | Ser | Trp | Asp | Ala<br>180 |

| Pro | Ala | Val | Thr | Val<br>185 | Arg | Tyr | Tyr | Arg | Ile<br>190 | Thr | Tyr | Gly | Glu | Thr<br>195 |

| Gly | Gly | Asn | Ser | Pro<br>200 | Val | Gln | Glu | Phe | Thr<br>205 | Val | Pro | Gly | Ser | Lys<br>210 |

| Ser | Thr | Ala | Thr | Ile<br>215 | Ser | Gly | Leu | Lys | Pro<br>220 | Gly | Val | Asp | Tyr | Thr<br>225 |

| Ile | Thr | Val | Tyr | Ala<br>230 | Val | Thr | Gly | Arg | Gly<br>235 | Asp | Ser | Pro | Ala | Ser<br>240 |

| Ser | Lys | Pro | Ile | Ser<br>245 | Ile | Asn | Tyr | Arg | Thr<br>250 | Glu | Ile | Asp | Lys | Pro<br>255 |

Ser ( 2 ) INFORMATION FOR SEQ ID NO:2:

( i ) SEQUENCE CHARACTERISTICS:
        ( A ) LENGTH: 266 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:

(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:2:

| Pro | Thr | Asp | Leu | Arg | Phe | Thr | Asn | Ile | Gly | Pro | Asp | Thr | Met | Arg |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Val | Thr | Trp | Ala | Pro | Pro | Pro | Ser | Ile | Asp | Leu | Thr | Asn | Phe | Leu |
|     |     |     |     | 20  |     |     |     |     | 25  |     |     |     |     | 30  |
| Val | Arg | Tyr | Ser | Pro | Val | Lys | Asn | Glu | Glu | Asp | Val | Ala | Glu | Leu |
|     |     |     |     | 35  |     |     |     |     | 40  |     |     |     |     | 45  |
| Ser | Ile | Ser | Pro | Ser | Asp | Asn | Ala | Val | Val | Leu | Thr | Asn | Leu | Leu |
|     |     |     |     | 50  |     |     |     |     | 55  |     |     |     |     | 60  |
| Pro | Gly | Thr | Glu | Tyr | Val | Val | Ser | Val | Ser | Ser | Val | Tyr | Glu | Gln |
|     |     |     |     | 65  |     |     |     |     | 70  |     |     |     |     | 75  |
| His | Glu | Ser | Thr | Pro | Leu | Arg | Gly | Arg | Gln | Lys | Thr | Gly | Leu | Asp |
|     |     |     |     | 80  |     |     |     |     | 85  |     |     |     |     | 90  |
| Ser | Pro | Thr | Gly | Ile | Asp | Phe | Ser | Asp | Ile | Thr | Ala | Asn | Ser | Phe |
|     |     |     |     | 95  |     |     |     |     | 100 |     |     |     |     | 105 |
| Thr | Val | His | Trp | Ile | Ala | Pro | Arg | Ala | Thr | Ile | Thr | Gly | Tyr | Arg |
|     |     |     |     | 110 |     |     |     |     | 115 |     |     |     |     | 120 |
| Ile | Arg | His | His | Pro | Glu | His | Phe | Ser | Gly | Arg | Pro | Arg | Glu | Asp |
|     |     |     |     | 125 |     |     |     |     | 130 |     |     |     |     | 135 |
| Arg | Val | Pro | His | Ser | Arg | Asn | Ser | Ile | Thr | Leu | Thr | Asn | Leu | Thr |
|     |     |     |     | 140 |     |     |     |     | 145 |     |     |     |     | 150 |
| Pro | Gly | Thr | Glu | Tyr | Val | Val | Ser | Ile | Val | Ala | Leu | Asn | Gly | Arg |
|     |     |     |     | 155 |     |     |     |     | 160 |     |     |     |     | 165 |
| Glu | Glu | Ser | Pro | Leu | Leu | Ile | Gly | Gln | Gln | Ser | Thr | Val | Ser | Asp |
|     |     |     |     | 170 |     |     |     |     | 175 |     |     |     |     | 180 |
| Val | Pro | Arg | Asp | Leu | Glu | Val | Val | Ala | Ala | Thr | Pro | Thr | Ser | Leu |
|     |     |     |     | 185 |     |     |     |     | 190 |     |     |     |     | 195 |
| Leu | Ile | Ser | Trp | Asp | Ala | Pro | Ala | Val | Thr | Val | Arg | Tyr | Tyr | Arg |
|     |     |     |     | 200 |     |     |     |     | 205 |     |     |     |     | 210 |
| Ile | Thr | Tyr | Gly | Glu | Thr | Gly | Gly | Asn | Ser | Pro | Val | Gln | Glu | Phe |
|     |     |     |     | 215 |     |     |     |     | 220 |     |     |     |     | 225 |
| Thr | Val | Pro | Gly | Ser | Lys | Ser | Thr | Ala | Thr | Ile | Ser | Gly | Leu | Lys |
|     |     |     |     | 230 |     |     |     |     | 235 |     |     |     |     | 240 |
| Pro | Gly | Val | Asp | Tyr | Thr | Ile | Thr | Val | Tyr | Ala | Val | Thr | Gly | Arg |
|     |     |     |     | 245 |     |     |     |     | 250 |     |     |     |     | 255 |
| Gly | Asp | Ser | Pro | Ala | Ser | Ser | Lys | Pro | Ile | Ser |     |     |     |     |
|     |     |     |     | 260 |     |     |     |     | 265 |     |     |     |     |     |

(2) INFORMATION FOR SEQ ID NO:3:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: polypeptide (iii) HYPOTHETICAL:

(iv) ANTI-SENSE:

(v) FRAGMENT TYPE:

(vi) ORIGINAL SOURCE:
        (A) ORGANISM:
        (B) STRAIN:

(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:3:

```
Pro Thr Asp Leu Arg Phe Thr Asn Ile Gly Pro Asp Thr Met Arg
 1               5                  10                  15

Val Thr Trp Ala Pro Pro Pro Ser Ile Asp Leu Thr Asn Phe Leu
                20                  25                  30

Val Arg Tyr Ser Pro Val Lys Asn Glu Glu Asp Val Ala Glu Leu
                35                  40                  45

Ser Ile Ser Pro Ser Asp Asn Ala Val Val Leu Thr Asn Leu Leu
                50                  55                  60

Pro Gly Thr Glu Tyr Val Val Ser Val Ser Ser Val Tyr Glu Gln
                65                  70                  75

His Glu Ser Thr Pro Leu Arg Gly Arg Gln Lys Thr Gly Leu Asp
                80                  85                  90

Ser Pro Thr Gly Ile Asp Phe Ser Asp Ile Thr Ala Asn Ser Phe
                95                 100                 105

Thr Val His Trp Ile Ala Pro Arg Ala Thr Ile Thr Gly Tyr Arg
               110                 115                 120

Ile Arg His His Pro Glu His Phe Ser Gly Arg Pro Arg Glu Asp
               125                 130                 135

Arg Val Pro His Ser Arg Asn Ser Ile Thr Leu Thr Asn Leu Thr
               140                 145                 150

Pro Gly Thr Glu Tyr Val Val Ser Ile Val Ala Leu Asn Gly Arg
               155                 160                 165

Glu Glu Ser Pro Leu Leu Ile Gly Gln Gln Ser Thr Val Ser Asp
               170                 175                 180

Val Pro Arg Asp Leu Glu Val Val Ala Ala Thr Pro Thr Ser Leu
               185                 190                 195

Leu Ile Ser Trp Asp Ala Pro Ala Val Thr Val Arg Tyr Tyr Arg
               200                 205                 210

Ile Thr Tyr Gly Glu Thr Gly Gly Asn Ser Pro Val Gln Glu Phe
               215                 220                 225
```

```
Thr  Val  Pro  Gly  Ser  Lys  Ser  Thr  Ala  Thr  Ile  Ser  Gly  Leu  Lys
               230                       235                           240

Pro  Gly  Val  Asp  Tyr  Thr  Ile  Thr  Val  Tyr  Ala  Val  Thr  Gly  Arg
               245                       250                           255

Gly  Asp  Ser  Pro  Ala  Ser  Ser  Lys  Pro  Ile  Ser  Ile  Asn  Tyr  Arg
               260                       265                           270

Thr  Glu  Ile  Asp  Lys  Pro  Ser
               275
```

( 2 ) INFORMATION FOR SEQ ID NO:4:

( i ) SEQUENCE CHARACTERISTICS:
        ( A ) LENGTH: 281 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:4:

```
Ala  Val  Pro  Pro  Pro  Thr  Asp  Leu  Arg  Phe  Thr  Asn  Ile  Gly  Pro
 1                    5                       10                       15

Asp  Thr  Met  Arg  Val  Thr  Trp  Ala  Pro  Pro  Pro  Ser  Ile  Asp  Leu
                    20                       25                           30

Thr  Asn  Phe  Leu  Val  Arg  Tyr  Ser  Pro  Val  Lys  Asn  Glu  Glu  Asp
                    35                       40                           45

Val  Ala  Glu  Leu  Ser  Ile  Ser  Pro  Ser  Asp  Asn  Ala  Val  Val  Leu
                    50                       55                           60
```

```
Thr  Asn  Leu  Leu  Pro  Gly  Thr  Glu  Tyr  Val  Val  Ser  Val  Ser  Ser
                    65                  70                            75

Val  Tyr  Glu  Gln  His  Glu  Ser  Thr  Pro  Leu  Arg  Gly  Arg  Gln  Lys
                    80                       85                       90

Thr  Gly  Leu  Asp  Ser  Pro  Thr  Gly  Ile  Asp  Phe  Ser  Asp  Ile  Thr
                    95                       100                      105

Ala  Asn  Ser  Phe  Thr  Val  His  Trp  Ile  Ala  Pro  Arg  Ala  Thr  Ile
                    110                      115                      120

Thr  Gly  Tyr  Arg  Ile  Arg  His  His  Pro  Glu  His  Phe  Ser  Gly  Arg
                    125                      130                      135

Pro  Arg  Glu  Asp  Arg  Val  Pro  His  Ser  Arg  Asn  Ser  Ile  Thr  Leu
                    140                      145                      150

Thr  Asn  Leu  Thr  Pro  Gly  Thr  Glu  Tyr  Val  Val  Ser  Ile  Val  Ala
                    155                      160                      165

Leu  Asn  Gly  Arg  Glu  Glu  Ser  Pro  Leu  Leu  Ile  Gly  Gln  Gln  Ser
                    170                      175                      180

Thr  Val  Ser  Asp  Val  Pro  Arg  Asp  Leu  Glu  Val  Val  Ala  Ala  Thr
                    185                      190                      195

Pro  Thr  Ser  Leu  Leu  Ile  Ser  Trp  Asp  Ala  Pro  Ala  Val  Thr  Val
                    200                      205                      210

Arg  Tyr  Tyr  Arg  Ile  Thr  Tyr  Gly  Glu  Thr  Gly  Gly  Asn  Ser  Pro
                    215                      220                      225

Val  Gln  Glu  Phe  Thr  Val  Pro  Gly  Ser  Lys  Ser  Thr  Ala  Thr  Ile
                    230                      235                      240

Ser  Gly  Leu  Lys  Pro  Gly  Val  Asp  Tyr  Thr  Ile  Thr  Val  Tyr  Ala
                    245                      250                      255

Val  Thr  Gly  Arg  Gly  Asp  Ser  Pro  Ala  Ser  Ser  Lys  Pro  Ile  Ser
                    260                      265                      270

Ile  Asn  Tyr  Arg  Thr  Glu  Ile  Asp  Lys  Pro  Ser
                    275                      280
```

( 2 ) INFORMATION FOR SEQ ID NO:5:

( i ) SEQUENCE CHARACTERISTICS:
        ( A ) LENGTH: 383 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:5:

```
Ala  Pro  Ile  Val  Asn  Lys  Val  Val  Thr  Pro  Leu  Ser  Pro  Pro  Thr
 1                  5                        10                        15

Asn  Leu  His  Leu  Glu  Ala  Asn  Pro  Asp  Thr  Gly  Val  Leu  Thr  Val
                    20                        25                        30

Ser  Trp  Glu  Arg  Ser  Thr  Thr  Pro  Asp  Ile  Thr  Gly  Tyr  Arg  Ile
                    35                        40                        45

Thr  Thr  Thr  Pro  Thr  Asn  Gly  Gln  Gln  Gly  Asn  Ser  Leu  Glu  Glu
                    50                        55                        60

Val  Val  His  Ala  Asp  Gln  Ser  Ser  Cys  Thr  Phe  Asp  Asn  Leu  Ser
                    65                        70                        75

Pro  Gly  Leu  Glu  Tyr  Asn  Val  Ser  Val  Tyr  Thr  Val  Lys  Asp  Asp
                    80                        85                        90

Lys  Glu  Ser  Val  Pro  Ile  Ser  Asp  Thr  Ile  Ile  Pro  Ala  Val  Pro
                    95                       100                       105

Pro  Pro  Thr  Asp  Leu  Arg  Phe  Thr  Asn  Ile  Gly  Pro  Asp  Thr  Met
                   110                       115                       120

Arg  Val  Thr  Trp  Ala  Pro  Pro  Pro  Ser  Ile  Asp  Leu  Thr  Asn  Phe
                   125                       130                       135

Leu  Val  Arg  Tyr  Ser  Pro  Val  Lys  Asn  Glu  Glu  Asp  Val  Ala  Glu
                   140                       145                       150

Leu  Ser  Ile  Ser  Pro  Ser  Asp  Asn  Ala  Val  Val  Leu  Thr  Asn  Leu
                   155                       160                       165

Leu  Pro  Gly  Thr  Glu  Tyr  Val  Val  Ser  Val  Ser  Ser  Val  Tyr  Glu
                   170                       175                       180

Gln  His  Glu  Ser  Thr  Pro  Leu  Arg  Gly  Arg  Gln  Lys  Thr  Gly  Leu
                   185                       190                       195

Asp  Ser  Pro  Thr  Gly  Ile  Asp  Phe  Ser  Asp  Ile  Thr  Ala  Asn  Ser
                   200                       205                       210

Phe  Thr  Val  His  Trp  Ile  Ala  Pro  Arg  Ala  Thr  Ile  Thr  Gly  Tyr
                   215                       220                       225

Arg  Ile  Arg  His  His  Pro  Glu  His  Phe  Ser  Gly  Arg  Pro  Arg  Glu
                   230                       235                       240

Asp  Arg  Val  Pro  His  Ser  Arg  Asn  Ser  Ile  Thr  Leu  Thr  Asn  Leu
                   245                       250                       255

Thr  Pro  Gly  Thr  Glu  Tyr  Val  Val  Ser  Ile  Val  Ala  Leu  Asn  Gly
                   260                       265                       270

Arg  Glu  Glu  Ser  Pro  Leu  Leu  Ile  Gly  Gln  Gln  Ser  Thr  Val  Ser
                   275                       280                       285

Asp  Val  Pro  Arg  Asp  Leu  Glu  Val  Val  Ala  Ala  Thr  Pro  Thr  Ser
                   290                       295                       300
```

```
Leu  Leu  Ile  Ser  Trp  Asp  Ala  Pro  Ala  Val  Thr  Val  Arg  Tyr  Tyr
              305                     310                          315

Arg  Ile  Thr  Tyr  Gly  Glu  Thr  Gly  Gly  Asn  Ser  Pro  Val  Gln  Glu
              320                     325                          330

Phe  Thr  Val  Pro  Gly  Ser  Lys  Ser  Thr  Ala  Thr  Ile  Ser  Gly  Leu
              335                     340                          345

Lys  Pro  Gly  Val  Asp  Tyr  Thr  Ile  Thr  Val  Tyr  Ala  Val  Thr  Gly
              350                     355                          360

Arg  Gly  Asp  Ser  Pro  Ala  Ser  Ser  Lys  Pro  Ile  Ser  Ile  Asn  Tyr
              365                     370                          375

Arg  Thr  Glu  Ile  Asp  Lys  Pro  Ser
              380
```

( 2 ) INFORMATION FOR SEQ ID NO:6:

( i ) SEQUENCE CHARACTERISTICS:
        ( A ) LENGTH: 155 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:6:

```
Met  Ala  Ala  Gly  Ser  Ile  Thr  Thr  Leu  Pro  Ala  Leu  Pro  Glu  Asp
 1                  5                    10                          15

Gly  Gly  Ser  Gly  Ala  Phe  Pro  Pro  Gly  His  Phe  Lys  Asp  Pro  Lys
                    20                   25                          30
```

```
Arg Leu Tyr Cys Lys Asn Gly Gly Phe Phe Leu Arg Ile His Pro
             35                  40                  45

Asp Gly Arg Val Asp Gly Val Arg Glu Lys Ser Asp Pro His Ile
             50                  55                  60

Lys Leu Gln Leu Gln Ala Glu Glu Arg Gly Val Val Ser Ile Lys
             65                  70                  75

Gly Val Cys Ala Asn Arg Tyr Leu Ala Met Lys Glu Asp Gly Arg
             80                  85                  90

Leu Leu Ala Ser Lys Cys Val Thr Asp Glu Cys Phe Phe Phe Glu
             95                 100                 105

Arg Leu Glu Ser Asn Asn Tyr Asn Thr Tyr Arg Ser Arg Lys Tyr
            110                 115                 120

Thr Ser Trp Tyr Val Ala Leu Lys Arg Thr Gly Gln Tyr Lys Leu
            125                 130                 135

Gly Ser Lys Thr Gly Pro Gly Gln Lys Ala Ile Leu Phe Leu Pro
            140                 145                 150

Met Ser Ala Lys Ser
            155
```

( 2 ) INFORMATION FOR SEQ ID NO:7:

( i ) SEQUENCE CHARACTERISTICS:
        ( A ) LENGTH: 155 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:7:

| | | | | | | | | | | | | | | |
|---|---|---|---|---|---|---|---|---|---|---|---|---|---|---|
|Met|Ala|Ala|Gly|Ser|Ile|Thr|Thr|Leu|Pro|Ala|Leu|Pro|Glu|Asp|
|1| | | |5| | | | |10| | | | |15|
|Gly|Gly|Ser|Gly|Ala|Phe|Pro|Pro|Gly|His|Phe|Lys|Asp|Pro|Lys|
| | | | |20| | | | |25| | | | |30|
|Arg|Leu|Tyr|Cys|Lys|Asn|Gly|Gly|Phe|Phe|Leu|Arg|Ile|His|Pro|
| | | | |35| | | | |40| | | | |45|
|Asp|Gly|Arg|Val|Asp|Gly|Val|Arg|Glu|Lys|Ser|Asp|Pro|His|Ile|
| | | | |50| | | | |55| | | | |60|
|Lys|Leu|Gln|Leu|Gln|Ala|Glu|Glu|Arg|Gly|Val|Val|Ser|Ile|Lys|
| | | | |65| | | | |70| | | | |75|
|Gly|Val|Cys|Ala|Asn|Arg|Tyr|Leu|Ala|Met|Lys|Glu|Asp|Gly|Arg|
| | | | |80| | | | |85| | | | |90|
|Leu|Leu|Ala|Ser|Lys|Cys|Val|Thr|Asp|Glu|Cys|Phe|Phe|Phe|Glu|
| | | | |95| | | | |100| | | | |105|
|Arg|Leu|Glu|Ser|Asn|Asn|Tyr|Asn|Thr|Tyr|Arg|Ser|Arg|Lys|Tyr|
| | | | |110| | | | |115| | | | |120|
|Thr|Ser|Trp|Tyr|Val|Ala|Leu|Arg|Arg|Thr|Gly|Gln|Tyr|Lys|Leu|
| | | | |125| | | | |130| | | | |135|
|Gly|Ser|Lys|Thr|Gly|Pro|Gly|Gln|Lys|Ala|Ile|Leu|Phe|Leu|Pro|
| | | | |140| | | | |145| | | | |150|
|Met|Ser|Ala|Lys|Ser| | | | | | | | | | |
| | | | |155| | | | | | | | | | |

( 2 ) INFORMATION FOR SEQ ID NO:8:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:

( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:8:

```
Pro Thr Asp Leu Arg Phe Thr Asn Ile Gly Pro Asp Thr Met Arg
 1               5                  10                  15

Val Thr Trp Ala Pro Pro Pro Ser Ile Asp Leu Thr Asn Phe Leu
                20              25                      30

Val Arg Tyr Ser Pro Val Lys Asn Glu Glu Asp Val Ala Glu Leu
                35              40                      45

Ser Ile Ser Pro Ser Asp Asn Ala Val Val Leu Thr Asn Leu Leu
                50              55                      60

Pro Gly Thr Glu Tyr Val Val Ser Val Ser Ser Val Tyr Glu Gln
                65              70                      75

His Glu Ser Thr Pro Leu Arg Gly Arg Gln Lys Thr Gly Leu Asp
                80              85                      90

Ser Pro Thr Gly Ile Asp Phe Ser Asp Ile Thr Ala Asn Ser Phe
                95              100                     105

Thr Val His Trp Ile Ala Pro Arg Ala Thr Ile Thr Gly Tyr Arg
                110             115                     120

Ile Arg His His Pro Glu His Phe Ser Gly Arg Pro Arg Glu Asp
                125             130                     135

Arg Val Pro His Ser Arg Asn Ser Ile Thr Leu Thr Asn Leu Thr
                140             145                     150

Pro Gly Thr Glu Tyr Val Val Ser Ile Val Ala Leu Asn Gly Arg
                155             160                     165

Glu Glu Ser Pro Leu Leu Ile Gly Gln Gln Ser Thr Val Ser Asp
                170             175                     180

Val Pro Arg Asp Leu Glu Val Val Ala Ala Thr Pro Thr Ser Leu
                185             190                     195

Leu Ile Ser Trp Asp Ala Pro Ala Val Thr Val Arg Tyr Tyr Arg
                200             205                     210

Ile Thr Tyr Gly Glu Thr Gly Gly Asn Ser Pro Val Gln Glu Phe
                215             220                     225

Thr Val Pro Gly Ser Lys Ser Thr Ala Thr Ile Ser Gly Leu Lys
                230             235                     240

Pro Gly Val Asp Tyr Thr Ile Thr Val Tyr Ala Val Thr Gly Arg
                245             250                     255

Gly Asp Ser Pro Ala Ser Ser Lys Pro Ile Ser Ile Asn Tyr Arg
                260             265                     270

Thr Glu Ile Asp Lys Pro Ser Met Ala Ala Gly Ser Ile Thr Thr
                275             280                     285

Leu Pro Ala Leu Pro Glu Asp Gly Gly Ser Gly Ala Phe Pro Pro
                290             295                     300

Gly His Phe Lys Asp Pro Lys Arg Leu Tyr Cys Lys Asn Gly Gly
                305             310                     315

Phe Phe Leu Arg Ile His Pro Asp Gly Arg Val Asp Gly Val Arg
                320             325                     330

Glu Lys Ser Asp Pro His Ile Lys Leu Gln Leu Gln Ala Glu Glu
                335             340                     345

Arg Gly Val Val Ser Ile Lys Gly Val Cys Ala Asn Arg Tyr Leu
```

|       |       |       |       | 350   |       |       |       |       | 355   |       |       |       |       | 360   |
|-------|-------|-------|-------|-------|-------|-------|-------|-------|-------|-------|-------|-------|-------|-------|
| Ala   | Met   | Lys   | Glu   | Asp   | Gly   | Arg   | Leu   | Leu   | Ala   | Ser   | Lys   | Cys   | Val   | Thr   |
|       |       |       |       | 365   |       |       |       |       | 370   |       |       |       |       | 375   |
| Asp   | Glu   | Cys   | Phe   | Phe   | Phe   | Glu   | Arg   | Leu   | Glu   | Ser   | Asn   | Asn   | Tyr   | Asn   |
|       |       |       |       | 380   |       |       |       |       | 385   |       |       |       |       | 390   |
| Thr   | Tyr   | Arg   | Ser   | Arg   | Lys   | Tyr   | Thr   | Ser   | Trp   | Tyr   | Val   | Ala   | Leu   | Lys   |
|       |       |       |       | 395   |       |       |       |       | 400   |       |       |       |       | 405   |
| Arg   | Thr   | Gly   | Gln   | Tyr   | Lys   | Leu   | Gly   | Ser   | Lys   | Thr   | Gly   | Pro   | Gly   | Gln   |
|       |       |       |       | 410   |       |       |       |       | 415   |       |       |       |       | 420   |
| Lys   | Ala   | Ile   | Leu   | Phe   | Leu   | Pro   | Met   | Ser   | Ala   | Lys   | Ser   |       |       |       |
|       |       |       |       | 425   |       |       |       |       | 430   |       |       |       |       |       |

( 2 ) INFORMATION FOR SEQ ID NO:9:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:9:

|       |       |       |       |       |       |       |       |       |       |       |       |       |       |       |
|-------|-------|-------|-------|-------|-------|-------|-------|-------|-------|-------|-------|-------|-------|-------|
| Pro   | Thr   | Asp   | Leu   | Arg   | Phe   | Thr   | Asn   | Ile   | Gly   | Pro   | Asp   | Thr   | Met   | Arg   |
| 1     |       |       |       | 5     |       |       |       |       | 10    |       |       |       |       | 15    |
| Val   | Thr   | Trp   | Ala   | Pro   | Pro   | Pro   | Ser   | Ile   | Asp   | Leu   | Thr   | Asn   | Phe   | Leu   |
|       |       |       |       | 20    |       |       |       |       | 25    |       |       |       |       | 30    |
| Val   | Arg   | Tyr   | Ser   | Pro   | Val   | Lys   | Asn   | Glu   | Glu   | Asp   | Val   | Ala   | Glu   | Leu   |

| | 35 | 40 | 45 |
|---|---|---|---|
| Ser Ile Ser Pro | Ser Asp Asn Ala | Val Val Leu Thr | Asn Leu Leu |
| | 50 | 55 | 60 |
| Pro Gly Thr Glu | Tyr Val Val Ser | Val Ser Val Tyr | Glu Gln |
| | 65 | 70 | 75 |
| His Glu Ser Thr | Pro Leu Arg Gly | Arg Gln Lys Thr | Gly Leu Asp |
| | 80 | 85 | 90 |
| Ser Pro Thr Gly | Ile Asp Phe Ser | Asp Ile Thr Ala | Asn Ser Phe |
| | 95 | 100 | 105 |
| Thr Val His Trp | Ile Ala Pro Arg | Ala Thr Ile Thr | Gly Tyr Arg |
| | 110 | 115 | 120 |
| Ile Arg His His | Pro Glu His Phe | Ser Gly Arg Pro | Arg Glu Asp |
| | 125 | 130 | 135 |
| Arg Val Pro His | Ser Arg Asn Ser | Ile Thr Leu Thr | Asn Leu Thr |
| | 140 | 145 | 150 |
| Pro Gly Thr Glu | Tyr Val Val Ser | Ile Val Ala Leu | Asn Gly Arg |
| | 155 | 160 | 165 |
| Glu Glu Ser Pro | Leu Leu Ile Gly | Gln Gln Ser Thr | Val Ser Asp |
| | 170 | 175 | 180 |
| Val Pro Arg Asp | Leu Glu Val Val | Ala Ala Thr Pro | Thr Ser Leu |
| | 185 | 190 | 195 |
| Leu Ile Ser Trp | Asp Ala Pro Ala | Val Thr Val Arg | Tyr Tyr Arg |
| | 200 | 205 | 210 |
| Ile Thr Tyr Gly | Glu Thr Gly Gly | Asn Ser Pro Val | Gln Glu Phe |
| | 215 | 220 | 225 |
| Thr Val Pro Gly | Ser Lys Ser Thr | Ala Thr Ile Ser | Gly Leu Lys |
| | 230 | 235 | 240 |
| Pro Gly Val Asp | Tyr Thr Ile Thr | Val Tyr Ala Val | Thr Gly Arg |
| | 245 | 250 | 255 |
| Gly Asp Ser Pro | Ala Ser Ser Lys | Pro Ile Ser Ile | Asn Tyr Arg |
| | 260 | 265 | 270 |
| Thr Glu Ile Asp | Lys Pro Ser Met | Ala Ala Gly Ser | Ile Thr Thr |
| | 275 | 280 | 285 |
| Leu Pro Ala Leu | Pro Glu Asp Gly | Gly Ser Gly Ala | Phe Pro Pro |
| | 290 | 295 | 300 |
| Gly His Phe Lys | Asp Pro Lys Arg | Leu Tyr Cys Lys | Asn Gly Gly |
| | 305 | 310 | 315 |
| Phe Phe Leu Arg | Ile His Pro Asp | Gly Arg Val Asp | Gly Val Arg |
| | 320 | 325 | 330 |
| Glu Lys Ser Asp | Pro His Ile Lys | Leu Gln Leu Gln | Ala Glu Glu |
| | 335 | 340 | 345 |
| Arg Gly Val Val | Ser Ile Lys Gly | Val Cys Ala Asn | Arg Tyr Leu |
| | 350 | 355 | 360 |
| Ala Met Lys Glu | Asp Gly Arg Leu | Leu Ala Ser Lys | Cys Val Thr |
| | 365 | 370 | 375 |
| Asp Glu Cys Phe | Phe Phe Glu Arg | Leu Glu Ser Asn | Asn Tyr Asn |
| | 380 | 385 | 390 |
| Thr Tyr Arg Ser | Arg Lys Tyr Thr | Ser Trp Tyr Val | Ala Leu Arg |
| | 395 | 400 | 405 |
| Arg Thr Gly Gln | Tyr Lys Leu Gly | Ser Lys Thr Gly | Pro Gly Gln |
| | 410 | 415 | 420 |
| Lys Ala Ile Leu | Phe Leu Pro Met | Ser Ala Lys Ser | |
| | 425 | 430 | |

( 2 ) INFORMATION FOR SEQ ID NO:10:

( i ) SEQUENCE CHARACTERISTICS:
    ( A ) LENGTH: 258 amino acids
    ( B ) TYPE: amino acid
    ( C ) STRANDEDNESS: single
    ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:10:

```
Pro Ser Ile Asp Leu Thr Asn Phe Leu Val Arg Tyr Ser Pro Val
 1               5                  10                  15

Lys Asn Glu Glu Asp Val Ala Glu Leu Ser Ile Ser Pro Ser Asp
                20                  25                  30

Asn Ala Val Val Leu Thr Asn Leu Leu Pro Gly Thr Glu Tyr Val
                35                  40                  45

Val Ser Val Ser Ser Val Tyr Glu Gln His Glu Ser Thr Pro Leu
                50                  55                  60

Arg Gly Arg Gln Lys Thr Gly Leu Asp Ser Pro Thr Gly Ile Asp
                65                  70                  75

Phe Ser Asp Ile Thr Ala Asn Ser Phe Thr Val His Trp Ile Ala
                80                  85                  90

Pro Arg Ala Thr Ile Thr Gly Tyr Arg Ile Arg His His Pro Glu
                95                  100                 105

His Phe Ser Gly Arg Pro Arg Glu Asp Arg Val Pro His Ser Arg
                110                 115                 120

Asn Ser Ile Thr Leu Thr Asn Leu Thr Pro Gly Thr Glu Tyr Val
                125                 130                 135
```

| | | | | | | | | | | | | |
|---|---|---|---|---|---|---|---|---|---|---|---|---|
|Val|Ser|Ile|Val|Ala|Leu|Asn|Gly|Arg|Glu|Glu|Ser|Pro|Leu|Leu|
| | | | |140| | | |145| | | | |150|

Val Ser Ile Val Ala Leu Asn Gly Arg Glu Glu Ser Pro Leu Leu
                    140                 145                         150

Ile Gly Gln Gln Ser Thr Val Ser Asp Val Pro Arg Asp Leu Glu
                    155                 160                         165

Val Val Ala Ala Thr Pro Thr Ser Leu Leu Ile Ser Trp Asp Ala
                    170                 175                         180

Pro Ala Val Thr Val Arg Tyr Tyr Arg Ile Thr Tyr Gly Glu Thr
                    185                 190                         195

Gly Gly Asn Ser Pro Val Gln Glu Phe Thr Val Pro Gly Ser Lys
                    200                 205                         210

Ser Thr Ala Thr Ile Ser Gly Leu Lys Pro Gly Val Asp Tyr Thr
                    215                 220                         225

Ile Thr Val Tyr Ala Val Thr Gly Arg Gly Asp Ser Pro Ala Ser
                    230                 235                         240

Ser Lys Pro Ile Ser Ile Asn Tyr Arg Thr Glu Ile Asp Lys Pro
                    245                 250                         255

Ser Gln Met ( 2 ) INFORMATION FOR SEQ ID NO:11:

( i ) SEQUENCE CHARACTERISTICS:
        ( A ) LENGTH: 279 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:11:

| | | | | | | | | | | | | | | |
|---|---|---|---|---|---|---|---|---|---|---|---|---|---|---|
| Pro | Thr | Asp | Leu | Arg | Phe | Thr | Asn | Ile | Gly | Pro | Asp | Thr | Met | Arg |
| 1 | | | | 5 | | | | | 10 | | | | | 15 |
| Val | Thr | Trp | Ala | Pro | Pro | Pro | Ser | Ile | Asp | Leu | Thr | Asn | Phe | Leu |
| | | | | 20 | | | | | 25 | | | | | 30 |
| Val | Arg | Tyr | Ser | Pro | Val | Lys | Asn | Glu | Glu | Asp | Val | Ala | Glu | Leu |
| | | | | 35 | | | | | 40 | | | | | 45 |
| Ser | Ile | Ser | Pro | Ser | Asp | Asn | Ala | Val | Val | Leu | Thr | Asn | Leu | Leu |
| | | | | 50 | | | | | 55 | | | | | 60 |
| Pro | Gly | Thr | Glu | Tyr | Val | Val | Ser | Val | Ser | Ser | Val | Tyr | Glu | Gln |
| | | | | 65 | | | | | 70 | | | | | 75 |
| His | Glu | Ser | Thr | Pro | Leu | Arg | Gly | Arg | Gln | Lys | Thr | Gly | Leu | Asp |
| | | | | 80 | | | | | 85 | | | | | 90 |
| Ser | Pro | Thr | Gly | Ile | Asp | Phe | Ser | Asp | Ile | Thr | Ala | Asn | Ser | Phe |
| | | | | 95 | | | | | 100 | | | | | 105 |
| Thr | Val | His | Trp | Ile | Ala | Pro | Arg | Ala | Thr | Ile | Thr | Gly | Tyr | Arg |
| | | | | 110 | | | | | 115 | | | | | 120 |
| Ile | Arg | His | His | Pro | Glu | His | Phe | Ser | Gly | Arg | Pro | Arg | Glu | Asp |
| | | | | 125 | | | | | 130 | | | | | 135 |
| Arg | Val | Pro | His | Ser | Arg | Asn | Ser | Ile | Thr | Leu | Thr | Asn | Leu | Thr |
| | | | | 140 | | | | | 145 | | | | | 150 |
| Pro | Gly | Thr | Glu | Tyr | Val | Val | Ser | Ile | Val | Ala | Leu | Asn | Gly | Arg |
| | | | | 155 | | | | | 160 | | | | | 165 |
| Glu | Glu | Ser | Pro | Leu | Leu | Ile | Gly | Gln | Gln | Ser | Thr | Val | Ser | Asp |
| | | | | 170 | | | | | 175 | | | | | 180 |
| Val | Pro | Arg | Asp | Leu | Glu | Val | Val | Ala | Ala | Thr | Pro | Thr | Ser | Leu |
| | | | | 185 | | | | | 190 | | | | | 195 |
| Leu | Ile | Ser | Trp | Asp | Ala | Pro | Ala | Val | Thr | Val | Arg | Tyr | Tyr | Arg |
| | | | | 200 | | | | | 205 | | | | | 210 |
| Ile | Thr | Tyr | Gly | Glu | Thr | Gly | Gly | Asn | Ser | Pro | Val | Gln | Glu | Phe |
| | | | | 215 | | | | | 220 | | | | | 225 |
| Thr | Val | Pro | Gly | Ser | Lys | Ser | Thr | Ala | Thr | Ile | Ser | Gly | Leu | Lys |
| | | | | 230 | | | | | 235 | | | | | 240 |
| Pro | Gly | Val | Asp | Tyr | Thr | Ile | Thr | Val | Tyr | Ala | Val | Thr | Gly | Arg |
| | | | | 245 | | | | | 250 | | | | | 255 |
| Gly | Asp | Ser | Pro | Ala | Ser | Ser | Lys | Pro | Ile | Ser | Ile | Asn | Tyr | Arg |
| | | | | 260 | | | | | 265 | | | | | 270 |
| Thr | Glu | Ile | Asp | Lys | Pro | Ser | Gln | Met | | | | | | |
| | | | | 275 | | | | | | | | | | |

( 2 ) INFORMATION FOR SEQ ID NO:12:

( i ) SEQUENCE CHARACTERISTICS:
    ( A ) LENGTH: 274 amino acids
    ( B ) TYPE: amino acid
    ( C ) STRANDEDNESS: single
    ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:

(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:12:

```
Pro Thr Asp Leu Arg Phe Thr Asn Ile Gly Pro Asp Thr Met Arg
 1               5                  10                  15

Val Thr Trp Ala Pro Pro Pro Ser Ile Asp Leu Thr Asn Phe Leu
                20                  25                  30

Val Arg Tyr Ser Pro Val Lys Asn Glu Glu Asp Val Ala Glu Leu
                35                  40                  45

Ser Ile Ser Pro Ser Asp Asn Ala Val Val Leu Thr Asn Leu Leu
                50                  55                  60

Pro Gly Thr Glu Tyr Val Val Ser Val Ser Ser Val Tyr Glu Gln
                65                  70                  75

His Glu Ser Thr Pro Leu Arg Gly Arg Gln Lys Thr Gly Leu Asp
                80                  85                  90

Ser Pro Thr Gly Ile Asp Phe Ser Asp Ile Thr Ala Asn Ser Phe
                95                  100                 105

Thr Val His Trp Ile Ala Pro Arg Ala Thr Ile Thr Gly Tyr Arg
                110                 115                 120

Ile Arg His His Pro Glu His Phe Ser Gly Arg Pro Arg Glu Asp
                125                 130                 135

Arg Val Pro His Ser Arg Asn Ser Ile Thr Leu Thr Asn Leu Thr
                140                 145                 150

Pro Gly Thr Glu Tyr Val Val Ser Ile Val Ala Leu Asn Gly Arg
                155                 160                 165

Glu Glu Ser Pro Leu Leu Ile Gly Gln Gln Ser Thr Val Ser Asp
                170                 175                 180

Val Pro Arg Asp Leu Glu Val Val Ala Ala Thr Pro Thr Ser Leu
                185                 190                 195

Leu Ile Ser Trp Asp Ala Pro Ala Val Thr Val Arg Tyr Tyr Arg
                200                 205                 210

Ile Thr Tyr Gly Glu Thr Gly Gly Asn Ser Pro Val Gln Glu Phe
                215                 220                 225

Thr Val Pro Gly Ser Lys Ser Thr Ala Thr Ile Ser Gly Leu Lys
```

|           |     |     |     | 230 |     |     |     | 235 |     |     |     | 240 |
|-----------|-----|-----|-----|-----|-----|-----|-----|-----|-----|-----|-----|-----|

Pro Gly Val Asp Tyr Thr Ile Thr Val Tyr Ala Val Thr Gly Arg
                245                 250                 255

Gly Asp Ser Pro Ala Ser Ser Lys Pro Ile Ser Ile Asn Tyr Arg
                260                 265                 270

Thr Glu Ile Asp ( 2 ) INFORMATION FOR SEQ ID NO:13:

( i ) SEQUENCE CHARACTERISTICS:
        ( A ) LENGTH: 283 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:13:

Ala Val Pro Pro Pro Thr Asp Leu Arg Phe Thr Asn Ile Gly Pro
 1               5                   10                  15

Asp Thr Met Arg Val Thr Trp Ala Pro Pro Ser Ile Asp Leu
                20              25                      30

Thr Asn Phe Leu Val Arg Tyr Ser Pro Val Lys Asn Glu Glu Asp
                35              40                      45

Val Ala Glu Leu Ser Ile Ser Pro Ser Asp Asn Ala Val Val Leu
                50              55                      60

Thr Asn Leu Leu Pro Gly Thr Glu Tyr Val Ser Val Ser Ser
                65              70                      75

| | | | | | | | | | | | | | |
|---|---|---|---|---|---|---|---|---|---|---|---|---|---|
|Val|Tyr|Glu|Gln|His 80|Glu|Ser|Thr|Pro|Leu 85|Arg|Gly|Arg|Gln|Lys 90|
|Thr|Gly|Leu|Asp|Ser 95|Pro|Thr|Gly|Ile|Asp 100|Phe|Ser|Asp|Ile|Thr 105|
|Ala|Asn|Ser|Phe|Thr 110|Val|His|Trp|Ile|Ala 115|Pro|Arg|Ala|Thr|Ile 120|
|Thr|Gly|Tyr|Arg|Ile 125|Arg|His|His|Pro|Glu 130|His|Phe|Ser|Gly|Arg 135|
|Pro|Arg|Glu|Asp|Arg 140|Val|Pro|His|Ser|Arg 145|Asn|Ser|Ile|Thr|Leu 150|
|Thr|Asn|Leu|Thr|Pro 155|Gly|Thr|Glu|Tyr|Val 160|Val|Ser|Ile|Val|Ala 165|
|Leu|Asn|Gly|Arg|Glu 170|Glu|Ser|Pro|Leu|Leu 175|Ile|Gly|Gln|Gln|Ser 180|
|Thr|Val|Ser|Asp|Val 185|Pro|Arg|Asp|Leu|Glu 190|Val|Val|Ala|Ala|Thr 195|
|Pro|Thr|Ser|Leu|Leu 200|Ile|Ser|Trp|Asp|Ala 205|Pro|Ala|Val|Thr|Val 210|
|Arg|Tyr|Tyr|Arg|Ile 215|Thr|Tyr|Gly|Glu|Thr 220|Gly|Gly|Asn|Ser|Pro 225|
|Val|Gln|Glu|Phe|Thr 230|Val|Pro|Gly|Ser|Lys 235|Ser|Thr|Ala|Thr|Ile 240|
|Ser|Gly|Leu|Lys|Pro 245|Gly|Val|Asp|Tyr|Thr 250|Ile|Thr|Val|Tyr|Ala 255|
|Val|Thr|Gly|Arg|Gly 260|Asp|Ser|Pro|Ala|Ser 265|Ser|Lys|Pro|Ile|Ser 270|
|Ile|Asn|Tyr|Arg|Thr 275|Glu|Ile|Asp|Lys|Pro 280|Ser|Gln|Met| | |

( 2 ) INFORMATION FOR SEQ ID NO:14:

( i ) SEQUENCE CHARACTERISTICS:
        ( A ) LENGTH: 385 amino acids
        ( B ) TYPE: amino acid
        ( C ) STRANDEDNESS: single
        ( D ) TOPOLOGY: linear ( i i ) MOLECULE TYPE: polypeptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:

(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:14:

```
Ala Pro Ile Val Asn Lys Val Val Thr Pro Leu Ser Pro Pro Thr
 1               5                  10                 15

Asn Leu His Leu Glu Ala Asn Pro Asp Thr Gly Val Leu Thr Val
                20                  25                 30

Ser Trp Glu Arg Ser Thr Thr Pro Asp Ile Thr Gly Tyr Arg Ile
                35                  40                 45

Thr Thr Thr Pro Thr Asn Gly Gln Gln Gly Asn Ser Leu Glu Glu
                50                  55                 60

Val Val His Ala Asp Gln Ser Ser Cys Thr Phe Asp Asn Leu Ser
                65                  70                 75

Pro Gly Leu Glu Tyr Asn Val Ser Val Tyr Thr Val Lys Asp Asp
                80                  85                 90

Lys Glu Ser Val Pro Ile Ser Asp Thr Ile Ile Pro Ala Val Pro
                95                 100                105

Pro Pro Thr Asp Leu Arg Phe Thr Asn Ile Gly Pro Asp Thr Met
               110                 115                120

Arg Val Thr Trp Ala Pro Pro Pro Ser Ile Asp Leu Thr Asn Phe
               125                 130                135

Leu Val Arg Tyr Ser Pro Val Lys Asn Glu Glu Asp Val Ala Glu
               140                 145                150

Leu Ser Ile Ser Pro Ser Asp Asn Ala Val Val Leu Thr Asn Leu
               155                 160                165

Leu Pro Gly Thr Glu Tyr Val Val Ser Val Ser Ser Val Tyr Glu
               170                 175                180

Gln His Glu Ser Thr Pro Leu Arg Gly Arg Gln Lys Thr Gly Leu
               185                 190                195

Asp Ser Pro Thr Gly Ile Asp Phe Ser Asp Ile Thr Ala Asn Ser
               200                 205                210

Phe Thr Val His Trp Ile Ala Pro Arg Ala Thr Ile Thr Gly Tyr
               215                 220                225

Arg Ile Arg His His Pro Glu His Phe Ser Gly Arg Pro Arg Glu
               230                 235                240

Asp Arg Val Pro His Ser Arg Asn Ser Ile Thr Leu Thr Asn Leu
               245                 250                255

Thr Pro Gly Thr Glu Tyr Val Val Ser Ile Val Ala Leu Asn Gly
               260                 265                270

Arg Glu Glu Ser Pro Leu Leu Ile Gly Gln Gln Ser Thr Val Ser
               275                 280                285

Asp Val Pro Arg Asp Leu Glu Val Val Ala Ala Thr Pro Thr Ser
               290                 295                300

Leu Leu Ile Ser Trp Asp Ala Pro Ala Val Thr Val Arg Tyr Tyr
               305                 310                315
```

| | | | | | | | | | | | | |
|---|---|---|---|---|---|---|---|---|---|---|---|---|
|Arg|Ile|Thr|Tyr|Gly|Glu|Thr|Gly|Gly|Asn|Ser|Pro|Val|Gln|Glu|
| | | | |320| | | | |325| | | | |330|
|Phe|Thr|Val|Pro|Gly|Ser|Lys|Ser|Thr|Ala|Thr|Ile|Ser|Gly|Leu|
| | | | |335| | | | |340| | | | |345|
|Lys|Pro|Gly|Val|Asp|Tyr|Thr|Ile|Thr|Val|Tyr|Ala|Val|Thr|Gly|
| | | | |350| | | | |355| | | | |360|
|Arg|Gly|Asp|Ser|Pro|Ala|Ser|Ser|Lys|Pro|Ile|Ser|Ile|Asn|Tyr|
| | | | |365| | | | |370| | | | |375|
|Arg|Thr|Glu|Ile|Asp|Lys|Pro|Ser|Gln|Met|
| | | | |380| | | | |385|

( 2 ) INFORMATION FOR SEQ ID NO:15:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:15:

CTATTACACC ATGGATGGTT TG    22

( 2 ) INFORMATION FOR SEQ ID NO:16:

( i ) SEQUENCE CHARACTERISTICS:
        ( A ) LENGTH: 26 bases
        ( B ) TYPE: nucleic acid
        ( C ) STRANDEDNESS: single ( D ) TOPOLOGY: linear ( i i ) MOLECULE TYPE: other nucleic acid ( i i i ) HYPOTHETICAL:

( i v ) ANTI-SENSE: No ( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION: /note="1-26 S primer"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:16:

CAGGACCATG GCAGCCGGGA GCATCA    26

( 2 ) INFORMATION FOR SEQ ID NO:17:

( i ) SEQUENCE CHARACTERISTICS:
    ( A ) LENGTH: 24 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL:

( i v ) ANTI-SENSE: Yes ( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:

(A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION: /note="1-24 S primer"

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:17:

AGCTTGATGT GAGGGTCGCT CTTC      24

(2) INFORMATION FOR SEQ ID NO:18:

(i) SEQUENCE CHARACTERISTICS:
                (A) LENGTH: 28 bases
                (B) TYPE: nucleic acid
                (C) STRANDEDNESS: single
                (D) TOPOLOGY: linear (ii) MOLECULE TYPE: other nucleic acid (iii) HYPOTHETICAL:

(iv) ANTI-SENSE: No (v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION: /note="1-28 S primer"

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:

(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:18:

CCTCACATCA AGCTACAACT TCAAGCAG    28

(2) INFORMATION FOR SEQ ID NO:19:

(i) SEQUENCE CHARACTERISTICS:
(A) LENGTH: 28 bases
(B) TYPE: nucleic acid
(C) STRANDEDNESS: single
(D) TOPOLOGY: linear (ii) MOLECULE TYPE: other nucleic acid (iii) HYPOTHETICAL:

(iv) ANTI-SENSE: Yes (v) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION: /note="1-28 S primer"

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:19:

CACATTTAGA AGCCAGTAAT CTTCCATC    28

(2) INFORMATION FOR SEQ ID NO:20:

(i) SEQUENCE CHARACTERISTICS:
(A) LENGTH: 28 bases
(B) TYPE: nucleic acid
(C) STRANDEDNESS: single
(D) TOPOLOGY: linear (ii) MOLECULE TYPE: other nucleic acid (iii) HYPOTHETICAL:

( i v ) ANTI-SENSE: No ( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION: /note="1-28 S primer"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:20:

GGCTTCTAAA TGTGTTACGG ATGAGTGT    28

( 2 ) INFORMATION FOR SEQ ID NO:21:

( i ) SEQUENCE CHARACTERISTICS:
    ( A ) LENGTH: 20 bases
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL:

( i v ) ANTI-SENSE: Yes ( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:

```
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION: /note="1-20 S primer"

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:21:

GTGAAATAAG CTTAGATGTG        20

( 2 ) INFORMATION FOR SEQ ID NO:22:

( i ) SEQUENCE CHARACTERISTICS:
                ( A ) LENGTH: 491 base pairs
                ( B ) TYPE: nucleic acid
                ( C ) STRANDEDNESS: double
                ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:22:
```

```
ATG GCA GCC GGG AGC ATC ACC ACG CTG CCC GCC TTG CCC GAG GAT      45
GGC GGC AGC GGC GCC TTC CCG CCC GGC CAC TTC AAG GAC CCC AAG      90
CGG CTG TAC TGC AAA AAC GGG GGC TTC TTC CTG CGC ATC CAC CCC     135
GAC GGC CGA GTT GAC GGG GTC CGG GAG AAG AGC GAC CCT CAC ATC     180
AAG CTA CAA CTT CAA GCA GAA GAG AGA GGA GTT GTG TCT ATC AAA     225
GGA GTG TGT GCT AAC CGT TAC CTG GCT ATG AAG GAA GAT GGA AGA     270
TTA CTG GCT TCT AAA TGT GTT ACG GAT GAG TGT TTC TTT TTT GAA     315
CGA TTG GAA TCT AAT AAC TAC AAT ACT TAC CGC TCA AGG AAA TAC     360
ACC AGT TGG TAT GTG GCA CTG AAA CGA ACT GGG CAG TAT AAA CTT     405
GGA TCC AAA ACA CGA CCT GGG CAG AAA GCT ATA CTT TTT CTT CCA     450
ATG TCT GCT AAG AGC TGATTTTAAT GGCCACATCT AAGCTT                491
```

( 2 ) INFORMATION FOR SEQ ID NO:23:

( i ) SEQUENCE CHARACTERISTICS:
        ( A ) LENGTH: 491 base pairs
        ( B ) TYPE: nucleic acid
        ( C ) STRANDEDNESS: double
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:23:

```
ATG GCA GCC GGG AGC ATC ACC ACG CTG CCC GCC TTG CCC GAG GAT      45
GGC GGC AGC GGC GCC TTC CCG CCC GGC CAC TTC AAG GAC CCC AAG      90
CGG CTG TAC TGC AAA AAC GGG GGC TTC TTC CTG CGC ATC CAC CCC     135
GAC GGC CGA GTT GAC GGG GTC CGG GAG AAG AGC GAC CCT CAC ATC     180
AAG CTA CAA CTT CAA GCA GAA GAG AGA GGA GTT GTG TCT ATC AAA     225
GGA GTG TGT GCT AAC CGT TAC CTG GCT ATG AAG GAA GAT GGA AGA     270
TTA CTG GCT TCT AAA TGT GTT ACG GAT GAG TGT TTC TTT TTT GAA     315
CGA TTG GAA TCT AAT AAC TAC AAT ACT TAC CGC TCA AGG AAA TAC     360
ACC AGT TGG TAT GTG GCA CTG AGA CGA ACT GGG CAG TAT AAA CTT     405
GGA TCC AAA ACA GGA CCT GGG CAG AAA GCT ATA CTT TTT CTT CCA     450
```

-continued

```
ATG TCT GCT AAG AGC TGATTTTAAT GGCCACATCT AAGCTT         491
```

POLYPEPTIDE HAVING HUMAN FIBRONECTIN-LIKE CELL ADHESIVE ACTIVITY

BACKGROUND OF THE INVENTION

1. Field of the Invention

This invention relates to a novel polypeptide, more particularly, to a novel functional polypeptide wherein a polypeptide having a cell-adhesive activity like that of human fibronectin is covalently bound to a human fibroblast growth factor.

2. Description of Related Art

It has been known that fibronectin (hereinafter referred to simply as FN) is a glycoprotein which is contained in the plasma and extracellular matrix and has various functions [Annual Review of Biochemistry, 57, 375-413 (1988)]. Thus, attempts have been made to apply natural FN to drugs such as vulnerary drugs or eye drops and to cosmetics. However none of these attempts has been successfully put into practice sine natural FN, being collected from the blood, is only restrictedly supplied and expensive and, furthermore, might be contaminated with, for example, pathogenic bacteria or viruses. These problems also make it impossible to put any functional domain isolated from natural FN into practice.

Under these circumstances, an artificial polypeptide having a cell-adhesive activity and an amino acid seqence of SEQ ID No: 10, an amino acid sequence of SEQ ID No: 11, an amino acid sequence of SEQ ID No: 12, an amino acid sequence of SEQ ID No: 13, and an amino acid sequence of SEQ ID No: 14 in the sequence listing and a method for producing the same by connecting a cDNA segment coding for a poly peptide derived from cell-binding domain of human FN to an expression vector were developed and applied for patent (U.S. Pat. No. 5,045,631, U.S. Pat. No. 5,102,988, U.S. Pat. No. 5,049,658, and U.S. Pat. No. 5,136,023). These polypeptides having a cell-adhesive activity and those expression vectors are summarized in table 1.

TABLE 1

| SEQ ID No | polypeptide | (amino acid residues) | expression vector | Patent No |
|---|---|---|---|---|
| No: 10 | Pro$^{1260}$-Met$^{1517}$ | (258) | pTF2021 | 5045631 |
| No: 11 | Pro$^{1239}$-Met$^{1517}$ | (279) | pTF7021 | 5045631 |
| No: 12 | Pro$^{1239}$-Asp$^{1512}$ | (274) | pTF7221 | 5102988 |
| No: 13 | Ala$^{1235}$-Met$^{1517}$ | (283) | pTF901 | 5049658 |
| No: 14 | Ala$^{1133}$-Met$^{1517}$ | (385) | pTFB800 | 5136023 |

In this specification, the numbers used to label the amino acids are the number of the amino acid residue from the N-terminal of the amino acid sequence obtained by translation of the cDNA sequence of FN in the EMBL Data Bank.

On the other hand, a fibroblast growth factor (hereinafter referred to simply as FGF) is a polypeptide having various biological actions, for example, a growth and differentiation promotion effect on various cells derived from the mesoderm and neuroectoderm, a chemotatic effect on endothelial cells, fibroblasts and astroglias, and a vascularization effect [Annual Review of Biochemistry, 58, 547-606(1989)]. Thus FGF is widely used as a growth factor for cell culture, and further it is expected to be applicable to medical materials such as a vulnerary based on the cell growth promoting, chemotactic and vascularization functions.

As described above, FGF is expected to exert a vulnerary effect based on the cell growth promotion, chemotactic and vascularization functions thereof. When a cell-adhesive activity is further added thereto, the affinity of FGF for various cells can be improved and hence the effects of FGF can be utilized to the fullest for a prolonged period of time, which is highly effective in the application of FGF to, for example, the development of drug delivery systems and sustained release drugs. For example, it makes it possible to provide growth promoting reagents useful in biochemical studies, cosmetics effective in enhancing the growth of epidermal cells and preventing skin aging, and endermic preparations remedies for promoting the healing of trauma or postoperational wounds.

A cell-adhesive polypeptide derived from FN and FGF polypeptide is a different kind of polypeptide derived from different source. As far as is known, a polypeptide containing both a cell-adhesive polypeptide and FGF polypeptide in a molecule was not known and moreover, a polypeptide having both activities in a polypeptide molecule is unexpected.

SUMMARY OF THE INVENTION

Accordingly, the present invention aims at providing a novel polypeptide having both a cell-adhesive activity like that of FN and a cell growth promoting activity like that of FGF.

In short, the present invention relates to an artificial functional polypeptide having a cell-adhesive activity and a fibroblast growth promoting activity and having the structure represented by the following formula [I]:

$$X—(Y)_m—Z \qquad [I]$$

wherein X is a polypeptide having a cell-adhesive activity, Y is a spacer, Z is a polypeptide having a fibroblast growth promoting activity, and m is 1 or 0.

The present inventors have studied a construction of a novel polypeptide having both of the cell-adhesive activity like that of FN and the cell growth promoting activity of FGF and a process for producing the same. As a result, we have prepared, through genetic engineering techniques, a novel functional polypeptide wherein a polypeptide derived from cell-binding domain of human FN is bound to human FGF.

Examination on the biological activities of this novel functional polypeptide indicates that it has both of the cell-adhesive activity and the cell growth promoting activity. The present invention has been thus completed.

Now the present invention will be described in greater detail.

The primary structure of human FN protein is described in The EMBO Journal, 4, 1755-1759 (1985). A cDNA clone (pLF5) coding for the cell-binding domain thereof is described in Biochemistry, 25, 4936-4941 (1986). A polypeptide having cell-adhesive activity and a process for producing the same were developed by isolating a cDNA segment for the cell-binding domain from pLF5, connecting said segment to an expression vector and introducing said vector into *E. coli* and a patent was applied for (refer to the patents cited in table 1). As the cDNA of the polypeptide having cell-adhesive activity required in the present invention, a recombinant plasmid pTF7021 described in table 1 may be used. This pTF7021 is a plasmid capable of expressing Pro$^{1239}$-Met$^{1517}$ of the cell-binding domain of FN, consisting of 279 amino acid residues and having an amino acid sequence of SEQ ID No: 11. Thus the cDNA for the polypeptide having an cell-adhesive activity and an amino acid sequence of SEQ ID No: 3 can be connected to a DNA coding for another polypeptide by introducing a cloning site, for example, NcoI site, immediately before the termination codon at the C-terminus of the translation region of pTF7021. The plasmid pTF7021 is prepared from *Escherichia coli* JM109/pTF7021 (FERM BP-1941). The oligo nucleotide fragment represented as SEQ ID No: 15 in the sequence listing is synthesized and a kit (site-directed mutagenesis system Mutan-K: Takara Shuzo) is used to achieve introduction of the NcoI site into pTF7021. With this introduction of NcoI site, the $Gln^{1516}$-$Met^{1517}$ of the C-terminal of the polypeptide of $Pro^{1239}$-$Met^{1517}$ is replaced by $Met^{1516}$-$Val^{1517}$. The plasmid thus prepared is designated pTF7520. By connecting a DNA coding for another polypeptide to NcoI site of pTF7520, a plasmid coding for a fusion polypeptide of the polypeptide having an amino acid sequence of SEQ ID No: 3 and another polypeptide is obtained. In the same way, the oligo nucleotide repersented as SEQ ID No: 15 in the sequence listing and the kit for site-directed mutagenesis are used to achieve introduction of the NcoI site into the each plasmid, pTF2021, pTF7221, pTF901, and pTFB800, shown in table 1. With the introduction of NcoI site to pTF2021, the cDNA for the polypeptide consisting of 256 amino acid residues corresponding to $Pro^{1260}$-$Ser^{1515}$ and having an amino acid sequence of SEQ ID No: 1 in the sequence listing can be connected to a NcoI site of DNA coding for another polypeptide using introduced NcoI site of plasmid. With the introduction of NcoI site to pTF7221, the cDNA for the polypeptide consisting of 266 amino acid residues corresponding to $Pro^{1239}$-$Ser^{1504}$ and having an amino acid sequence of SEQ ID No: 2 in the sequence listing can be connected to a NcoI site of DNA coding for another polypeptide using introduced NcoI site of plasmid. With the introduction of NcoI site to pTF901, the cDNA for the polypeptide consisting of 281 amino acid residues corresponding to $Ala^{1235}$-$Ser^{1515}$ and having an amino acid sequence of SEQ ID No: 4 in the sequence listing can be connected to a NcoI site of DNA coding for another polypeptide using introduced NcoI site of plasmid. With the introduction of NcoI site to pTFB800, the cDNA for the polypeptide consisting of 383 amino acid residues corresponding to $Ala^{1133}$-$Ser^{1515}$ and an amino acid sequence of SEQ ID No: 5 in the sequence listing can be connected to a NcoI site DNA coding for another polypeptide using introduced NcoI site of plasmid.

FGF involves acidic FGF (hereinafter referred to simply as aFGF), basic FGF (hereinafter referred to simply as bFGF), etc. The polypeptide of the present invention can be obtained by connecting the above mentioned cDNA for the polypeptide having cell-adhesive activity with a DNA coding for FGF, followed by expression through genetic engineering techniques.

Examples of the novel functional polypeptide according to the present invention include an artificial functional polypeptide, wherein a polypeptide consisting of 277 amino acid residues corresponding to $Pro^{1239}$-$Ser^{1515}$ of the cell-binding domain of human FN, and having an amino acid sequence of SEQ ID No: 3 in the sequence listing, is bound to human bFGF having an amino acid sequence of SEQ ID No: 6 in the sequence listing.

The gene structure of human bFGF consisting of three exons has been clarified [The EMBO Journal, 5, 2523-2528 (1986)]. A DNA segment for each exon can be amplified from a human genomic DNA by PCR [Polymerase Chain Reaction: Saiki et al., Science, 230, 1350-1354 (1985)]. When the terminal sequence of the adjacent exon is introduced into the 5'-side of the PCR primer thus obtained, it is possible to connect exon segments, which are amplified separately, to each other by PCR. More specifically, the antisense sequence of a DNA coding for the N-terminus of the second exon is introduced into the 5'-side of the antisence primer for amplifying the first exon. When PCR is effected by using the resultant primer and the sense primer for amplifying the first exon, the first exon DNA segment, wherein the N-terminal sequence of the second exon is added to the 3'-terminus of the sense chain, is obtained. Similarly, the sense sequence of DNA coding for the C-terminus of the first exon is introduced into the 5'-side of the sense primer for amplifying the second exon. When PCR is effected with the use of the resultant primer and the antisense primer for amplifying the second exon, the second exon DNA segment, wherein the C-terminal sequence of the first exon is added to the 5'-terminus of the sense chain, is obtained. Subsequently, these two DNA segments thus obtained are mixed together and PCR is effected with the use of the sense primer for amplifying the first exon and the antisense primer for amplifying the second exon to thereby give a novel DNA segment wherein the first exon is bound to the second exon. The DNA segment coding for the first and second exons is then bound to another DNA segment for the third exon in the same manner as the one described above to obtain a DNA segment coding for the full length of human bFGF.

When NcoI and HindIII segments of the DNA coding for human bFGF obtained above are prepared and connected to the 3'-terminal NcoI site of the translational region of a plasmid pTF7520 derived from the above-mentioned plasmid pTF7021, a recombinant plasmid pYMH-CF.A, capable of expressing the polypeptide having an amino acid sequence of SEQ ID No: 8 in the sequence listing, wherein the polypeptide having cell-adhesive activity like that of FN and having an amino acid sequence of SEQ ID No: 3 in the sequence listing is connected to human bFGF having an amino acid sequence of SEQ ID No: 6 in the sequence listing, can be obtained (refer to FIG. 1). In FIG. 1, A represents a DNA fragment coding for the human bFGF polypeptide while B represents a DNA fragment coding for the polypeptide having cell-adhesive activity derived from human FN cell-binding domain. The intermolecular distance between the polypeptide having cell-adhesive activity and the human bFGF polypeptide can be controlled by inserting a linker DNA into the connection site of these DNA fragment and expressing the same as a spacer polypeptide. Either an amino acid or a polypeptide may be inserted between these molecules as a spacer. The amino acid and the sequence of the polypeptide to be used as a spacer may be appropriately selected depending on the purpose.

The amplification products of the DNA coding for human bFGF thus obtained through PCR involve, for example, a polypeptide having an amino acid sequence of SEQ ID No: 7 in the sequence listing, i.e., DNA coding for a point mutant of human FGF. By using this DNA, a recombinant plasmid pYMH-CF capable of expressing the polypeptide having an amino acid sequence of SEQ IN No: 9 in the sequence listing, wherein the polypeptide having an amino acid sequence of SEQ ID No: 3 in the sequence listing is connected to the polypeptide having an amino acid sequence of the SEQ ID No: 7 in the sequence listing, can be obtained.

Using the NcoI site introduced plasmid derived from pTF2021 and NcoI and HindIII segment of the DNA coding for human bFGF, a recombinant plasmid, capable of expressing the polypeptide, wherein the polypeptide having an amino acid sequence of SEQ ID No: 1 in the sequencce listing is connected to human bFGF polypeptide having an amino acid sequence of SEQ ID No: 6 or SEQ ID No: 7 in the sequence listing, can be obtained.

Using the NcoI site introduced plasmid derived from pTF7221 and NcoI and HindIII segment of the DNA coding for human bFGF, a recombinant plasmid, capable of expressing the polypeptide, wherein the polypeptide having an amino acid sequence of SEQ ID No: 2 in the sequence listing is connected to human bFGF polypeptide having an amino acid sequence of SEQ ID No: 6 or SEQ ID No: 7 in the sequence listing, can be obtained.

Using the NcoI site introduced plasmid derived from pTF901 and NcoI and HindIII segment of the DNA coding for human bFGF, a recombinant plasmid, capable of expressing the polypeptide, wherein the polypeptide having an amino acid sequence of SEQ ID No: 4 in the sequence listing is connected to human bFGF polypeptide having an amino acid sequence of SEQ ID No: 6 or SEQ ID No: 7 in the sequence listing, can be obtained.

Using the NcoI site introduced plasmid derived from pTFB800 and NcoI and HindIII segment of the DNA coding for human bFGF, a recombinant plasmid, capable of expressing the polypeptide, wherein the polypeptide having an amino acid sequence of SEQ ID No: 5 in the sequence listing is connected to human bFGF polypeptide having an amino acid sequence of SEQ ID No: 6 or SEQ ID No: 7 in the sequence listing, can be obtained.

The plasmid thus obtained is introduced into *E. coli* and incubated under appropriate conditions so as to accumulate the target polypeptide in *E. coli* cells. The expression is confirmed by immunoblotting. All of the cellular proteins of the recombinant *E coli* are separated by SDS polyacrylamide gel electrophoresis. Then the electrophoretic pattern is transferred onto a nitrocellulose membrane. A band detected with a monoclonal antibody capable of recognizing the human FN cell-binding domain, for example FN12-8 (Takara Shuzo) and another monoclonal antibody capable of recognizing human bFGF, for example bFM-2 [Proc. Natl. Acad. Sci. USA, 86, 8911-9915 (1989)] and Anti-FGF-Bosic (Sigma), corresponds to the target polypeptide.

The target polypeptide may be purified, for example, as follows. The recombinant *E. coli* cells are cultured in a medium such as L-broth, collected, and sonicated to thereby give a ground cell suspension. This suspension is centrifuged and after removing nucleic acids by adding polyethyleneimine, the supernatant is purified by, for example, Sephadex G-100 gel filtration column chromatography or heparin affinity column chromatography. Thus the target polypeptide can be obtained in a purified state.

The polypeptide obtained above is employed in the determination of cell-adhesive activity for Swiss mouse 3T3 or BALB/c 3T3 cells. The cell-adhesive activity may be determined in accordance with, for example, a method of Ruoslahti et al. [Methods in Enzymology, 82, 803-831 (1981)].

More specifically, a microtiter plate is coated with a sample and then blocked with BSA. Next, a suspension of Swiss mouse 3T3 or BALB/c 3T3 cells is added thereto and incubated at 37° C. for about 1 hour. After washing away unadsorbed cells, the adsorbed cells are recovered by trypsinization and counted with a Coulter counter. Thus the strength of cell-adhesive activity can be measured.

On the other hand, the FGF activity can be determined by measuring the $^3$H-thymidine uptake, which can be regarded as an indicator of fibroblast growth promoting activity, in accordance with, for example, a method of Nishikawa et al. [Methods in Enzymology, 146, 11-23 (1987)].

More specifically, a sample is added to a medium and BALB/c 3T3 cells are incubated therein for 16 hours. Next, $^3$H-thymidine is added thereto and the incubation is continued for additional 3 hours. The cells are then immobilized with trichloroacetic acid and solubilized with an alkali. Then the $^3$H-thymidine incorporated into the cells is measured with a liquid scintillation counter. Thus the fibroblast growth promoting activity as FGF can be determined.

On the other hand, the polypeptide of this invention has a cell growth promoting activity to human blood vessel endothelial cell. The effect on human blood vessel endothelial cells can be determined as follows.

More specifically, human blood vessel cells suspended in a medium containing 10% of fetal bovine serum are added in a plate which coated with sample and are incubated at 37° C. Cells are recovered at various times by trypsinization and counted with a Coulter counter. Thus the human blood vessel endothelial cell growth promoting activity can be determined.

EXAMPLES

Figure 1:
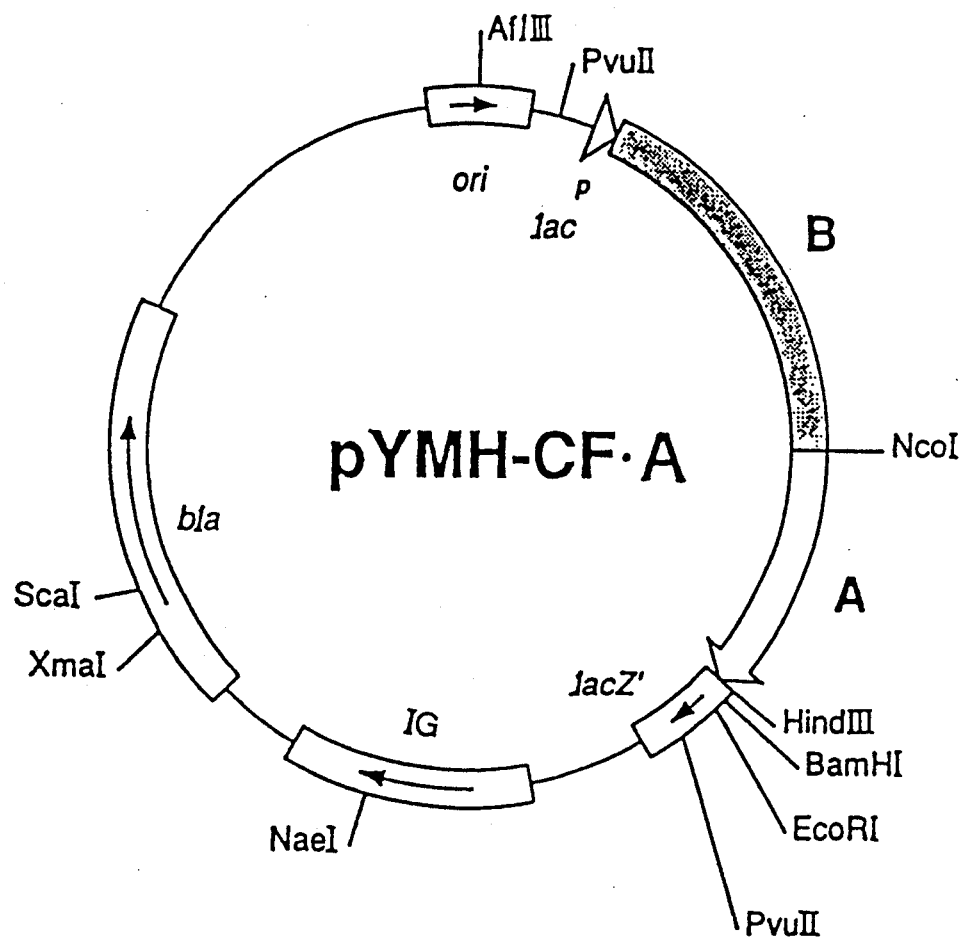
FIG. 1 shows the structure of pYMH-CF.A.

The following examples further illustrate the invention but are not intended to limit its scope.

EXAMPLE 1

Cloning of fused polypeptide comprising a polypeptide derived from human FN cell-binding domain polypeptide and a human bFGF polypeptide:

(1-1) Preparation of DNA coding for human bFGF polypeptide.

The following three pairs of primers were synthesized on a DNA synthesizer, purified, and subjected to PCR by using human brain genomic DNA as a template.

(i) Primers (1) and (2)

Primers (1) and (2) made it possible to amplify human bFGF exon 1. Bases No. 8 to No. 26 of the primer (1) having a DNA sequence of SEQ ID No: 16 in the sequence listing corresponded to a DNA sequence for the exon 1, while bases No. 6 to No. 11 corresponded to a DNA sequence coding for the NcoI site and bases No. 8 to No. 10 corresponded to DNA sequence coding for the N-terminal Met of bFGF. Further, bases No. 8 to No. 24 of the primer (2) having a DNA sequence of SEQ ID No: 17 in the sequence listing corresponded to the anti-sense DNA sequence of the exon 1, while bases No. 1 to No. 7 corresponded to the antisense DNA sequence of the exon 2 and bases No. 1 to No. 14 corresponded to a DNA sequence overlapping the primer (3) as will be described hereinbelow.

(ii) Primers (3) and (4)

Primers (3) and (4) made it possible to amplify human bFGF exon 2. Bases No. 8 to No. 28 of the primer (3) having a DNA sequence of SEQ ID No: 18 in the sequence list corresponded to a DNA sequence for the exon 2, while bases No. 1 to No. 7 corresponded to a DNA sequence of the exon 1. Bases No. 1 to No. 14 corresponded to a DNA sequence overlapping the primer (2). Further, bases No. 8 to No. 28 of the primer (4) having a DNA sequence of SEQ ID No: 19 in the sequence listing corresponded to the antisense DNA sequence of the exon 2, while bases No. 1 to No. 7 corresponded to the antisense DNA sequence of the exon 3 and bases No. 1 to No. 14 corresponded to a DNA sequence overlapping the primer (5) as will be described herein below.

(iii) Primers (5) and (6)

Primers (5) and (6) made it possible to amplify human bFGF exon 3. Bases No. 8 to No. 28 of the primer (5) having a DNA sequence of SEQ ID No: 20 in the sequence listing corresponded to a DNA sequence for the exon 3, while bases No. 1 to No. 7 corresponded to a DNA sequence of the exon 2 and bases No. 1 to No. 14 corresponded to a DNA sequence overlapping the primer (4). The primer (6) having a DNA sequence of SEQ ID No: 21 in the sequence listing was the antisense DNA sequence of the exon (3) wherein the bases No. 8 and No. 11 had been changed from G to A and from A to C, respectively, so as to make the sequence of the bases No. 8 to No. 13 serve as the Hind III site for cloning.

PCR was carried out by using a GeneAmp Kit (Takara Shuzo). 1 μg of the template DNA and 100 μl of a reaction solution were employed and a temperature cycle (94° C. for 30 seconds, 55° C. for 1 minute and 72° C. for 2 minutes) was repeated 30 times. One-twentieth of the reaction solution was analyzed by agarose gel electrophoresis to observe DNA segments of 192 bp [amplified with primers (1) and (2)], 118 bp [amplified with primers (3) and (4)] and 223 bp [amplified with primers (5) and (6)], which respectively corresponded to the human bFGF exons 1, 2, and 3.

A mixture of 1 μl of the PCR product of the exon 1 with 1 μl of that of the exon 2 was used as a template to effect PCR of the primers (1) and (4) by repeating a temperature cycle (94° C. for 30 seconds, 55° C. for 1 minute and 72° C. for 1 minute) 30 times. Thus a DNA segment of 296 bp, wherein the exon 1 was connected to the exon 2, was obtained.

A mixture of 1 μl of this DNA segment with 1 μl of the PCR product of the exon 3 obtained above was used to effect PCR of the primers (1) and (6) by repeating a temperature cycle (94° C. for 30 seconds, 55° C. for 1 minute and 72° C. for 1 minute) 30 times. Thus an amplified DNA segment of 505 bp involving all of the code regions of the exons 1 to 3 was obtained. Next, this DNA segment was treated with NcoI and HindIII and then ligated to the NcoI, HindIII site of a plasmid pUC119N at 16° C. for 30 minutes by using a Ligation Kit (Takara Shuzo). Then the plasmid thus obtained was subjected to cloning and DNA analysis. A plasmid having a DNA sequence of SEQ ID No: 22 in the sequence listing integrated therein was named pYMH-bF.A, while another plasmid having a DNA sequence of SEQ ID No: 23 in the sequence listing integrated therein was named pYMH-bF. Further, *E. coli* JM109 (using Competent Cell JM109: Takara Shuzo) transformed with the plasmid pYMH-bF.A and the plasmid pYMH-bF were respectively named *Escherichia coli* JM109/pYMH-bF.A and *Escherichia coli* JM109/pYMH-bF.

(1-2) Cloning of fused polypeptide comprising a polypeptide derived from human FN cell-binding domain and a human bFGF polypeptide The plasmid pYMH-bF.A obtained in the above item (1-1) was treated with NcoI and HindIII so as to excise the DNA segment inserted therein. Then this DNA segment was ligated to the NcoI, HindIII site of the above-mentioned pTF7520 at 16° C. for 30 minutes. The plasmid thus constructed was named pYMH-CF.A and then *E. coli* JM109 was transformed therewith. The *E. coli* JM109 strain carrying this plasmid was named *Escherichia coli* JM109/pYMH-CF.A.

This strain was then incubated in an L-broth containing 50 μg/ml of ampicillin and 1 mM of isopropyl thio-β-D-galactoside (IPTG) and then analyzed with 4/20% SDS-PAGE. As a result, the expression of a polypeptide (molecular weight: 47 kd) was confirmed.

Further, the electrophoretic pattern was transferred onto a nitrocellulose membrane and treated with a monoclonal antibody FN12-8 capable of specifically recognizing a human FN cell-binding domain or another monoclonal antibody bFM-2 capable of specifically recognizing bFGF. Thus it was confirmed that both of these antibodies reacted with the polypeptide of 47 kd.

The *E. coli* JM109 strain carrying pYMH-CF A was indicated as *Escherichia coli* JM109/pYMH-CF.A and deposited with Fermentation Research Institute under the accession number FERM P-12637.

On the other hand, the plasmid pYMH-bF was treated with NcoI and HindIII to thereby excise the DNA segment inserted therein. Then this DNA segment was ligated to the NcoI, HindIII site of pTF7520 at 16° C. for 30 minutes. The plasmid thus constructed was named pYMH-CF and *E. coli* JM109 was transformed therewith. The plasmid contained in the transformant thus obtained was analyzed by the same method as the one described above, and the *E. coli* JM109 strain carrying the plasmid containing the target sequence was named *Escherichia coli* JM109/pYMH-CF.

The ability of this strain to express the target polypeptide was confirmed by the same method a the one described above. This strain was indicated as *Escherichia coli* JM109/pYMH-CF and deposited with Fermentation Research Institute under the accession number FERM P-12559.

(1-3) Purification of expressed polypeptide

The *Escherichia coli* JM109/pYMH-CF.A (FERM P-12637) obtained in the above item (1-2) was incubated in 10 ml of an L-broth containing 50 μg/ml of ampicillin at 37° C. overnight. 0.2 ml of this preincubation broth was inoculated into 100 ml of an L-broth containing 50 μg/ml of ampicillin and 1 mM of IPTG and incubated at 37° C. overnight. Then the cells were collected and suspended in 5 ml of a buffer solution [20 mM Tris-HCl (pH 7.6), 1 mM EDTA, 0.1% CHAPS [3-{3-cholamidopropyl)dimethylammonio}-1-propanesulfonic acid], 8M urea, 100 μg/ml aprotinin, 100 μg/ml leupeptin, and 100 mM PMSF (phenylmethanesulfonyl fluoride)]. The obtained suspension was sonicated for 2 minutes to thereby break up the cells. The sonicated suspension was centrifuged and supernatant was saved. Then 5% of polyethyleneimine was added to the saved solution at the ratio of 1 ml per 4000 OD260 units of solution and kept for 30 minutes at 4° C. with stirring. Then supernatant was obtained by centrifucation and applied to a Sephadex G-100 gel filtration column equilibrated with a buffer solution [20 mM Tris-HCl (pH 7.6), 1 mM EDTA, and 0.1% CHAPS]. Next, a fraction containing the target polypeptide of 47 kd was identified by SDS-polyacrylamide gel electrophoresis. This fraction was applied to a heparin-5PW HPLC column (Tosoh) equilibrated with the same buffer solution and then eluted with another buffer solution [500 mM NaCl, 20 mM Tris-Cl (pH 7.6), 1 mM EDTA, and 0.1% CHAPS]. The obtained eluate was subjected to SDS-polyacrylamide electrophoresis to confirm the target polypeptide as a single band of 47 kd. The target polypeptide thus purified was named C-FGF.A.

The *Escherichia coli* JM109/pYMH-CF (FERM P-12559) was incubated in the same manner and the target polypeptide was purified from the culture broth. The obtained polypeptide was named C-FGF.

EXAMPLE 2

Determination of Biological Activities

By using the polypeptides C-FGF.A and C-FGF obtained in the above Example 1, cell-adhesive activities and cell growth promoting activities were determined.

(2-1) Determination of cell-adhesive activity

The cell-adhesive activities were determined in accordance with the method of Ruoslahti et al. Namely, a sample was dissolved in, for example, distilled water or a phosphate-buffered physiological saline solution (PBS) and poured into a 24-well microtiter plate. Then the sample was adsorbed on the plate by incubating at room temperature for 2 hours (400 μl/well). The plate was blocked after adding 500 μl/well of a PBS solution containing 2% of bovine serum albumin (BSA) and incubated at 37° C. for 2 hours. Next, the plate was washed with PBS and $1 \times 10^5$ cells/well of Swiss mouse 3T3 cells, which had been previously suspended in Dulbeccos's minimum Eagle medium (DMEM), was added thereto for incubating at 37° C. for 1 hour. The Swiss mouse 3T3 cells employed herein were ones obtained by subculturing a frozen cell strain and trypsinizing at 37° C. for 5 minutes. After washing the plate with PBS, the adsorbed cells were collected through trypsinization and counted with a Coulter counter.

As a result, the C-FGF.A and C-FGF showed each a cell-adhesive activity comparable to that of a cell-adhesion active polypeptide C274 [Pro$^{1239}$-Asp$^{1512}$ (274 amino acid residues) having an amino acid sequence of SEQ ID No: 12 in the sequence listing: U.S. Pat. No. 5,102,988].

(2-2) Determination of cell growth promoting activity

The cell growth promoting activities of the C-FGF.A and C-FGF, each of which showed a cell-adhesive activity in the above item (2-1), were examined.

(A) Fibloblast growth promoting activity $6.25 \times 10^3$ cells/well of mouse fibroblast BALB/c 3T3/3K cells suspended in Dulbeccos's minimum Eagle medium containing 3% of calf serum (3% CS-DMEM) were poured into a 24-well microtiter plate and incubated in the presence of 5% of $CO_2$ at 37° C. for 5 hours. Then the medium was replaced with DMEM containing 0.2% of calf serum (0.2% CS-DMEM) to continue incubation at 37° C. for additional 24 hours. Next, the C-FGF.A, C-FGF or C274 was added thereto and incubated at 37° C. for 16 hours. After adding 0.2 μCi/well of $^3$H-thymidine, the incubation was further continued at 37° C. for 3 hours. Then the medium was removed and 500 μl/well of 5% TCA was added, followed by allowing to stand at 4° C. for 4 hours to thereby immobilize the cells. After removing the TCA, 400 μl/well of 0.1N NaOH containing 2% of $Na_2CO_3$ was added to dissolve the immobilized cells therein. Then the $^3$H-thymidine uptake was measured with a liquid scintillation counter. As table 2 shows, a high $^3$H-thymidine uptake, namely, a fibloblast growth promoting activity was observed when each of the C-FGF.A and the C-FGF was used.

TABLE 2

| Sample (100 nM) | H-thymidine uptake ($\times 10^3$ cpm) |
| --- | --- |
| C-FGF.A | 2.4 |
| C-FGF | 1.8 |
| C274 | 0.5 |

(B) Human blood vessel endothelial cell growth promoting activity

Using human blood vessel endothelial cells, the cell growth promoting activity of polypeptide of this invention was examined.

400 μl of 1 μM C-FGF.A or 1 μM C274 was poured into a 24-well microtiter plate, and adsorbed on the plate by incubating at 37° C. for 2 hours. After washing the plate with PBS, $1.8 \times 10^4$ cells of human blood vessel endothelial cells, which had been previously suspended in MCDB-104(GK) medium containing 10% of fetal bovine serum, was added to each well for incubating in the presence of 5% $CO_2$ at 37° C. After 2 hours, 4 days, 6 days, or 8 days the cells in well were collected through trypsinization and counted with a Coulter counter.

As shown in table 3, a remarkable increase of cells was observed when C-FGF.A was used. The polypeptide of this invention had a strong growth promoting activity of human blood vessel endothelial cells.

TABLE 3

| | cell number ($\times 10^3$) | | | |
| --- | --- | --- | --- | --- |
| sample | 2 hour | Day 4 | Day 6 | Day 8 |
| C-FGF.A | 4.6 | 5.5 | 10.5 | 11.3 |
| C274 | 3.3 | 1.5 | 1.7 | 0.4 |

As described above, the present invention provides a functional polypeptide having both of a cell-adhesive activity and a cell growth promoting activity and a process for producing the same.

The above-mentioned polypeptide, which can elevate the affinity of FGF for cells, is highly useful, in particular, for vulnerary purposes.

What we claim is:

1. An artificial functional polypeptide having a cell-adhesive activity and a fibroblast growth activity, and having the structure represented by the following formula:

X—Z wherein X is a polypeptide having an amino acid sequence of SEQ ID No: 3, and Z is a polypeptide having an amino acid sequence of SEQ ID No: 6 or SEQ ID No: 7.

* * * * *